(12) United States Patent
Sugawara

(10) Patent No.: US 10,149,705 B2
(45) Date of Patent: Dec. 11, 2018

(54) SPINE IMMOBILIZATION TOOL

(71) Applicant: AKITA PREFECTURAL HOSPITAL ORGANIZATION, Akita-shi, Akita (JP)

(72) Inventor: Taku Sugawara, Akita (JP)

(73) Assignee: AKITA PREFECTURAL HOSPITAL ORGANIZATION, Akita-shi, Akita (JP)

( * ) Notice: Subject to any disclaimer, the term of this patent is extended or adjusted under 35 U.S.C. 154(b) by 0 days.

(21) Appl. No.: 15/098,820

(22) Filed: Apr. 14, 2016

(65) Prior Publication Data

US 2016/0228158 A1    Aug. 11, 2016

Related U.S. Application Data

(63) Continuation of application No. 14/128,225, filed as application No. PCT/JP2012/065765 on Jun. 20, 2012, now abandoned.

(30) Foreign Application Priority Data

Jun. 20, 2011 (JP) ................................. 2011-136665

(51) Int. Cl.
*A61B 17/70* (2006.01)
*A61B 17/80* (2006.01)
(Continued)

(52) U.S. Cl.
CPC ...... *A61B 17/7068* (2013.01); *A61B 17/8085* (2013.01); *A61B 2017/568* (2013.01); *A61B 2034/108* (2016.02); *A61F 2002/449* (2013.01)

(58) Field of Classification Search
CPC ............ A61B 17/7044; A61B 17/7047; A61B 17/7062; A61B 17/7065; A61B 17/7067;
(Continued)

(56) References Cited

U.S. PATENT DOCUMENTS 4,611,582 A    9/1986 Duff
5,007,909 A    4/1991 Rogozinski
(Continued)

FOREIGN PATENT DOCUMENTS

JP    2003-038507 A    2/2003
JP    2004-184606 A    7/2004
(Continued)

OTHER PUBLICATIONS

International Search Report dated Jul. 24, 2012; PCT/JP2012/065765.
(Continued)

*Primary Examiner* — Ellen C Hammond
(74) *Attorney, Agent, or Firm* — Ladas & Parry LLP

(57) ABSTRACT

A spine immobilization tool that can control the movement of the spine with improved safety as a spine immobilization tool that includes a first covering portion, a second covering portion, and a joint portion. The first covering portion covers at least a part of a vertebral arch of a vertebra at a head-side among the adjacent vertebrae, and thus can be fixed to the vertebra. The second covering portion covers at least a part of a vertebral arch of a vertebra at a buttock side amongst the adjacent vertebrae, and thus can be fixed to the vertebra. The joint portion couples the first covering portion and the second covering portion together while allowing changing relative positions of the first covering portion and the second covering portion.

7 Claims, 7 Drawing Sheets

(51) Int. Cl.
  *A61B 17/56* (2006.01)
  *A61B 34/10* (2016.01)
  *A61F 2/44* (2006.01)

(58) Field of Classification Search
  CPC .............. A61B 17/7068; A61B 17/707; A61B 17/7071; A61B 17/8038; A61B 17/8042
  See application file for complete search history.

(56) References Cited

U.S. PATENT DOCUMENTS

| | | | |
|---|---|---|---|
| 6,613,050 | B1 | 9/2003 | Wagner et al. |
| 7,029,472 | B1 | 4/2006 | Fortin |
| 7,238,204 | B2 | 7/2007 | Le Couedic et al. |
| 7,837,688 | B2 | 11/2010 | Boyer, II et al. |
| 8,048,118 | B2 | 11/2011 | Lim et al. |
| 8,246,680 | B2 * | 8/2012 | Betz .................. A61F 2/30942 606/130 |
| 8,328,848 | B2 | 12/2012 | Lowery et al. |
| 8,419,772 | B2 | 4/2013 | Thompson et al. |
| 8,435,268 | B2 * | 5/2013 | Thompson .......... A61B 17/7002 606/248 |
| 8,470,000 | B2 | 6/2013 | Trautwein et al. |
| 8,623,062 | B2 * | 1/2014 | Kondrashov ...... A61B 17/7044 606/246 |
| 8,790,380 | B2 | 7/2014 | Buttermann |
| 8,968,365 | B2 | 3/2015 | Aschmann et al. |
| 2003/0109882 | A1 | 6/2003 | Shirado et al. |
| 2004/0175686 | A1 | 9/2004 | Ono et al. |
| 2006/0271055 | A1 | 11/2006 | Thramann |
| 2007/0161993 | A1 * | 7/2007 | Lowery .............. A61B 17/7055 606/279 |
| 2007/0270812 | A1 | 11/2007 | Peckham |
| 2008/0188945 | A1 * | 8/2008 | Boyce ................ A61B 17/0401 623/23.61 |
| 2008/0262552 | A1 * | 10/2008 | Kim .................... A61B 17/7011 606/276 |
| 2008/0294200 | A1 | 11/2008 | Kohm et al. |
| 2009/0105766 | A1 * | 4/2009 | Thompson ......... A61B 17/7002 606/279 |
| 2009/0270918 | A1 | 10/2009 | Attia et al. |
| 2009/0292314 | A1 | 11/2009 | Mangione et al. |
| 2011/0137353 | A1 | 6/2011 | Buttermann |
| 2011/0218571 | A1 | 9/2011 | Attia |
| 2013/0218208 | A1 | 8/2013 | Khoury |
| 2014/0316467 | A1 | 10/2014 | Siegal et al. |

FOREIGN PATENT DOCUMENTS

| | | |
|---|---|---|
| JP | 2007-307394 A | 11/2007 |
| JP | 2009-533167 A | 9/2009 |
| WO | 2010/011535 A1 | 1/2010 |

OTHER PUBLICATIONS

USPTO NFOA dated Apr. 3, 2015 in connection with U.S. Appl. No. 14/128,225.

USPTO FOA dated Dec. 14, 2015 in connection with U.S. Appl. No. 14/128,225.

\* cited by examiner

SPINE IMMOBILIZATION TOOL

TECHNICAL FIELD

The present invention relates to a spine immobilization tool that can control movement of a spine.

BACKGROUND ART

In a condition involving instability and deformation of a spine, for example, spondylosis deformans, scoliosis, and spinal injury, a spinal fixation surgery using a titanium-made implant is widely performed. The spinal fixation surgery is a surgery for inserting or fixing, for example, the titanium-made implant to the spine so as to improve the stability by fixing the spine.

The tools for fixing the spine includes, for example, a device disclosed in Patent Document 1. Patent Document 1 discloses a device to correct the spine for fixation. This device includes a spinal rod, a spinal hook and a bone screw for fixing the spinal rod to a vertebra such as a thoracic spine or a lumbar spine.

Patent Document 1: Japanese Unexamined Patent Application Publication No. 2007-307394

DISCLOSURE OF THE INVENTION

Problems to be Solved by the Invention

In the spinal fixation surgery, damage to a blood vessel or to a nerve due to mistake of the insertion position when the spinal fixation screw as one type of the implants is inserted into the spine is especially problematic. Additionally, fixing the spine may have a problem that mechanical stress occurs between adjacent vertebrae, thus causing additional lesion (referred to as lesion between the vertebrae including, for example, spondylolisthesis, spondylosis deformans, and hernia of intervertebral disk). The conventional technique requiring the spinal fixation screw is a technique for fixing individual vertebrae by a structure of a wood screw or similar screw. The spinal fixation screw may be pulled out after surgery. Also in the above technique disclosed in Patent Document 1, a bone screw is inserted into the spine, therefore, problem similar to the above-described problem may occur.

An object of the present invention is to provide a spine immobilization tool that can control the movement of the spine with improved safety.

Solutions to the Problems

Hereinafter, the present invention will be described.

The present invention is a spine immobilization tool for controlling movement of a spine by being mounted on a plurality of vertebrae. The spine immobilization tool includes a covering portion and a joint portion. The covering portion is fixable to the vertebra by covering at least a part of a vertebral arch of the vertebra for the respective plurality of vertebrae. The joint portion couples adjacent covering portions such that a relative position between the adjacent covering portions can be changed. The covering portion includes two or more members that each includes a close-contact surface. The close-contact surface is a surface that has a shape in a male-female relationship with a surface shape of the vertebral arch, and can be in close contact with the vertebral arch.

In the present invention, "joint portion" means a portion that has mobility to allow appropriately changing the relative positions between the adjacent covering portions and can couple the adjacent covering portions together. Here, "mobility to allow appropriately changing" means mobility to the extent that the mobility can be determined as necessary corresponding to the medical condition or similar condition of the patient when using the spine immobilization tool of the present invention. That is, this means that the joint portion has mobility to the extent that the mobility does not apply excessive mechanical stress between adjacent vertebrae while solving the instability with pathological significance. For example, the range of motion of the joint portion can be adjusted or fixed corresponding to the medical condition. A joint of the joint portion can be manufactured from artificial material typified by, for example, metal, ceramic, or polyethylene. One joint portion can be constituted by one joint or a combination of a plurality of joints. The expression of "the close-contact surface is a surface that has a shape in a male-female relationship with a surface shape of the vertebral arch, and can be in close contact with the vertebral arch" means that the close-contact surface is a surface shaped precisely conforming to the concavo-convex shape of the surface of the vertebral arch. This close-contact surface can be shaped precisely conforming to the concavo-convex shape of three-dimensional shape data of the vertebral arch after the data is obtained using computer tomography (CT). Here, the expression of "precisely conforming to" means that, in the case where the close-contact surface is brought into actual contact with the concavo-convex shape of the vertebral arch, the vertebral arch is in contact with 80% or more, more preferably, 90% or more, further preferably, 95% or more of the close-contact surface, or the error between the shape of the vertebral arch and the shape of the close-contact surface is equal to or less than 2 mm. The respective vertebral arches of the plurality of vertebrae have mutually different surface shapes. Accordingly, the close-contact surface has a varied shape for each covering portion.

In the spine immobilization tool of the present invention, preferably, the covering portion includes two members, and the covering portion is fixable to the vertebra by sandwiching the vertebral arch between the two members.

Here, the expression of "the covering portion includes two members, and the covering portion is fixable to the vertebra by sandwiching the vertebral arch between the two members" means that at least one covering portion among the plurality of covering portions in the spine immobilization tool includes two members and can be fixed to the vertebra by sandwiching the vertebral arch using these two members. With this configuration, covering at least a part of the vertebral arch by the covering portion facilitates fixing the covering portion to the vertebra.

In the spine immobilization tool of the present invention, preferably, the covering portion at a head side of the adjacent covering portions includes a first head-side member that covers a head side of the vertebral arch and a first buttock-side member that covers a buttock side of the vertebral arch. The covering portion at a buttock side of the adjacent covering portions preferably includes a second head-side member that covers the head side of the vertebral arch and a second buttock-side member that covers the buttock side of the vertebral arch. The first buttock-side member, the second head-side member, and the joint portion are preferably integrated together. The joint portion couples the first buttock-side member and the second head-side member together.

Here, the expression of "the covering portion at a head side of the adjacent covering portions includes a first head-side member that covers the head side of the vertebral arch and a first buttock-side member that covers a buttock side of the vertebral arch. The covering portion at the buttock side of the adjacent covering portions preferably includes a second head-side member that covers the head side of the vertebral arch and a second buttock-side member that covers the buttock side of the vertebral arch" means that, in at least one combination of the adjacent covering portions among the plurality of covering portions in the spine immobilization tool, the covering portion at the head side includes the first head-side member that covers the head side of the vertebral arch and the first buttock-side member that covers the buttock side of the vertebral arch. The covering portion at the buttock side includes the second head-side member that covers the head side of the vertebral arch and the second buttock-side member that covers the buttock side of the vertebral arch. With this configuration, integration of the first buttock-side member, the second head-side member, and the joint portion facilitates attaching and removing the covering portion to/from the vertebra and facilitates coupling the covering portions together by the joint portion.

In the spine immobilization tool of the present invention, preferably, the covering portions each includes a head-side member that covers the head side of the vertebral arch and a buttock-side member that covers the buttock side of the vertebral arch. Assuming that a covering portion fixable to a vertebra closest to the head side among the vertebrae to which the covering portions are fixed is a first covering portion and a covering portion fixable to an n-th vertebra (here, n is a natural number equal to or more than 2) from the head side among the vertebrae to which the covering portions are fixed is an n-th covering portion, the buttock-side member of an n'-th covering portion (here, n' is a natural number from 1 to n−1), the head-side member of an (n'+1)-th covering portion, and the joint portion are preferably integrated together. The joint portion couples the buttock-side member of the n'-th covering portion and the head-side member of the (n'+1)-th covering portion together.

All the covering portions included in the spine immobilization tool include the head-side member that covers the head side of the vertebral arch and the buttock-side member that covers the buttock side of the vertebral arch. In all the adjacent covering portions, the buttock-side member of one covering portion, the head-side member of another covering portion, and the joint portion that couples the buttock-side member and the head-side member are integrated together. Accordingly, even in the case where the number of the covering portions is large, this facilitates attaching and removing the respective covering portions to/from the vertebrae and facilitates coupling these covering portions by the joint portions.

In the spine immobilization tool of the present invention, a configuration where the covering portion and the joint portion are separately shaped, and the joint portion is removably attachable to the covering portion is also preferred.

Separately shaping the covering portion and the joint portion allows firstly fixing the covering portion to the vertebra and then coupling the adjacent covering portions together by the joint portion. For example, a plurality of covering portions that are independently shaped are fixed to the respective vertebrae, and the autologous bone permanently fixes the covering portions to the vertebrae after a lapse of a predetermined time period. Subsequently, the adjacent covering portions can be coupled by the joint portion.

In the spine immobilization tool of the present invention, preferably, the covering portion includes a portion in a mesh-like or sponge-like shape in a portion including the close-contact surface.

Here, the term of "mesh-like" means a structure with a plurality of holes that pass through from the surface (the close-contact surface) on the vertebral arch side covered with the covering portion to the surface on the opposite side in the covering portion. The term of "sponge-like" means a structure where a plurality of fine cavities is shaped inside of the covering portion, and may have a structure where these cavities are irregularly continuously formed. The configuration that includes the portion in this mesh-like or sponge-like shape results in shaping of fine unevenness on the close-contact surface of the covering portion, thus improving the fixity when the covering portion is mounted on the vertebral arch.

In the spine immobilization tool of the present invention, preferably, the covering portion employs osteoinductive matrix in the close-contact surface and the portion shaped in the mesh-like or sponge-like shape.

Here, the expression of "employs osteoinductive matrix in the close-contact surface" means that a layer including the osteoinductive matrix is shaped on the surface of the close-contact surface. The expression of "employs osteoinductive matrix in the portion shaped in the mesh-like or sponge-like shape" means that the osteoinductive matrix is included in the surface or the inside of the through-hole constituting the mesh-like structure, or the surface or the inside of the cavity constituting the sponge-like structure. Here, "osteoinductive matrix" means a bone prosthetic material or a bone regeneration-promoting substance with a bone regeneration-inducing effect. Materials known as the "bone prosthetic material" includes: a material that has already been approved as medical equipment in Japan for use in a bone defect portion, has approximately the same component with that of the autologous bone, and gradually adhered to and integrated with the autologous bone (for example, hydroxyapatite); and a material that is replaced by the autologous bone (for example, beta-tricalcium phosphate (bTCP)). Materials known as the "bone regeneration-promoting substances" include, for example, bone morphogenetic protein (BMP) as a substance that has the effect of promoting the bone formation. With the configuration where the close-contact surface of the covering portion and the portion shaped in the mesh-like or sponge-like shape employ the osteoinductive matrix, bone formation occurs on the surface of the covering portion by the effect of the osteoinductive matrix. This integrates the covering portion and the vertebra together, thus facilitating permanent fixation.

In the spine immobilization tool of the present invention, preferably, the covering portion is shaped by a selective laser sintering method.

Shaping the covering portion by the selective laser sintering method allows manufacturing the covering portion in a short period of time at low cost.

The spine immobilization tool of the present invention is preferred to include a fixing member to fix the covering portion to the vertebra.

The covering portion of the spine immobilization tool of the present invention includes the close-contact surface that has the shape in a male-female relationship with the surface shape of the vertebral arch and can be brought into close contact with the vertebral arch. This close-contact surface is brought into close contact with the vertebral arch such that the covering portion is fixed to the vertebra. In addition, the configuration that includes the fixing member for fixing the covering portion to the vertebra allows more strongly fixing the covering portion to the vertebra.

Effects of the Invention

With the spine immobilization tool of the present invention, fixing the plurality of covering portions coupled by the joint portion to the respective vertebrae allows controlling the movement of the spine. With the spine immobilization tool of the present invention, the respective close-contact surfaces of the covering portions are shaped corresponding to the surface shapes of the vertebral arches and the close-contact surface is brought into close contact with the vertebral arch. Thus, the covering portion is fixed to the vertebra. That is, the spine immobilization tool of the present invention allows fixing the covering portion to the vertebra without the spinal fixation screw that is required in the conventional technique. Accordingly, the spine immobilization tool of the present invention does not require, for example, screwing the vertebra, thus ensuring high safety and preventing occurrence of additional lesion. When the spinal fixation screw is used for assistance, the number of the spinal fixation screws can be reduced compared with the conventional number, and depth of insertion can also be reduced compared with the conventional depth. This ensures high safety and prevents occurrence of additional lesion.

DESCRIPTION OF PREFERRED EMBODIMENTS

Figure 1:
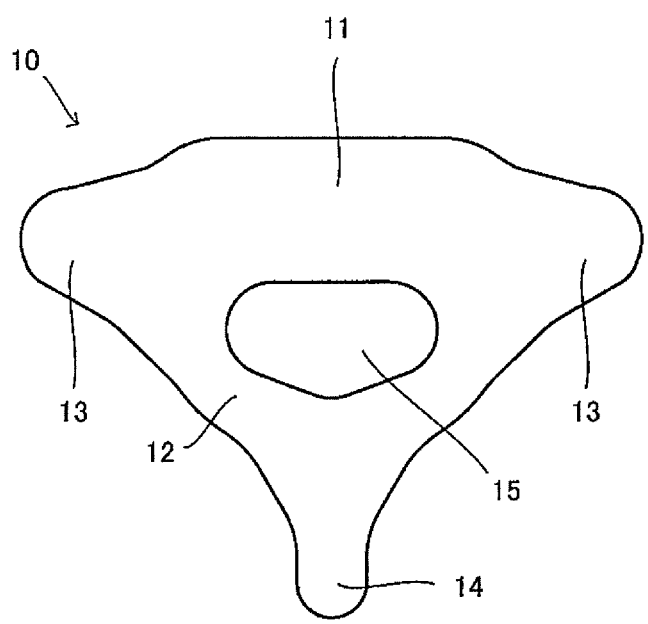
FIG. 1 is a plan view schematically illustrating one vertebra 10.

The above-described operation and advantages of the present invention are made apparent from the following description of embodiments. Hereinafter, the present invention will be described based on embodiments illustrated in the drawings. However, the present invention is not limited to these embodiments. The respective drawings are simplified for ease of illustration and understanding. Like reference numerals designate corresponding or identical elements throughout the various drawings, and repetitive reference numerals are omitted if necessary.

Prior to the description of a spine immobilization tool of the present invention, a spine will be briefly described. The spine is constituted by a string of a plurality of vertebrae. FIG. 1 is a plan view schematically illustrating one vertebra 10. In FIG. 1, the upper side indicates the ventral side, the lower side indicates the back side, the near side indicates the head side, and the far side indicates the buttock side on the plane of paper. The vertebra 10 includes a vertebral body 11 and a vertebral arch 12. The vertebral body 11 is on the ventral side and has a shape close to an oval shape. The vertebral arch 12 is disposed at the back side of the vertebral body 11. A spinous process 14 is disposed at the back side of the vertebral arch 12 while transverse processes 13 and 13 are disposed at the right and left sides of the vertebral arch 12. Between the vertebral body 11 and the vertebral arch 12, a vertebral foramen 15 is formed and a spinal cavity passes through the vertebral foramen 15. In the cervical spine, the thoracic spine, and the lumbar spine, the vertebral body 11 has approximately the same shape while the vertebral arches 12 each has a complicated varied shape. The spine immobilization tool of the present invention can be used mounted on the vertebral arch 12 as described below. While in the drawings the cervical spine is exemplarily illustrated, the spine immobilization tool of the present invention can be also mounted on any vertebral arch of the cervical spine, the thoracic spine, and the lumbar spine.

(Spine Immobilization Tool 50)

Figure 2:
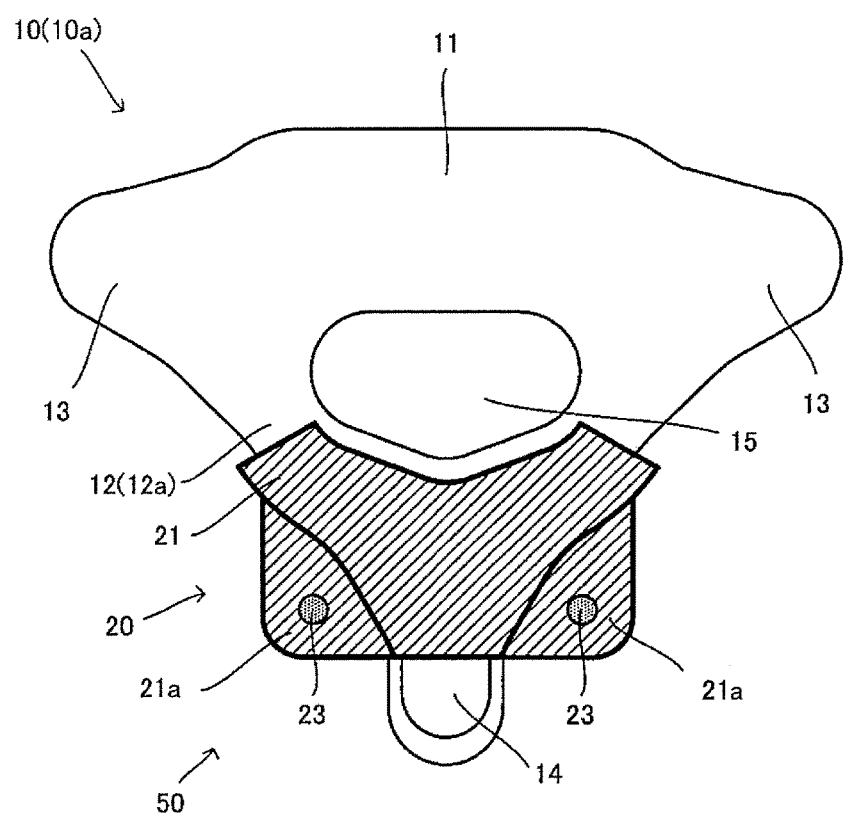
FIG. 2 is a plan view schematically illustrating a spine immobilization tool 50 at a posture in which it is mounted on the vertebrae 10 and 10.
Figure 3:
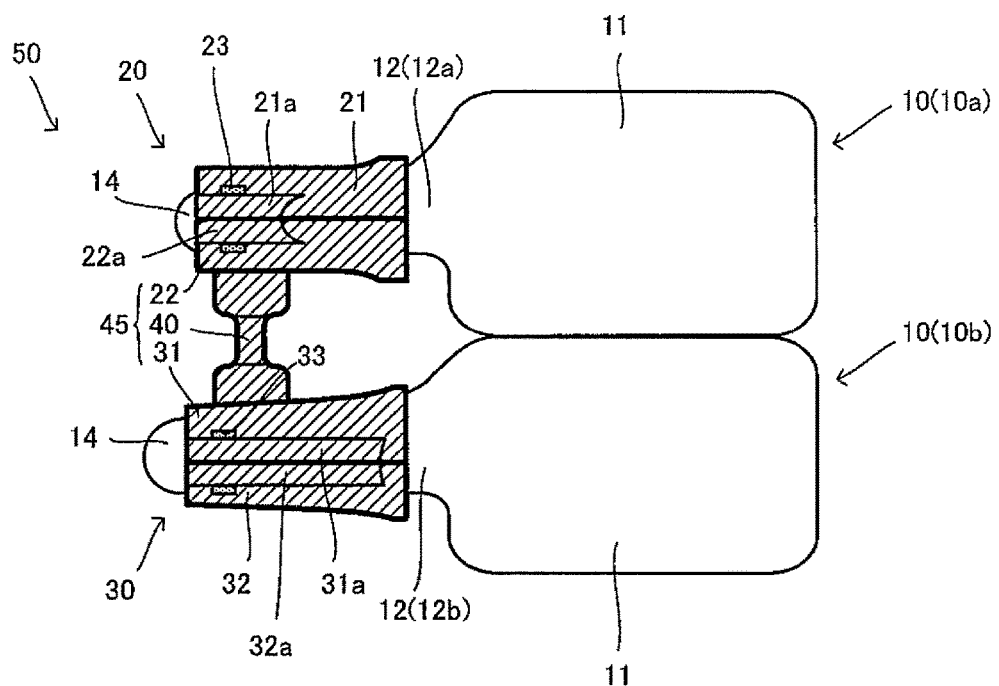
FIG. 3 is a side view schematically illustrating the spine immobilization tool 50 at the posture in which it is mounted on the vertebrae 10 and 10.
Figure 4:
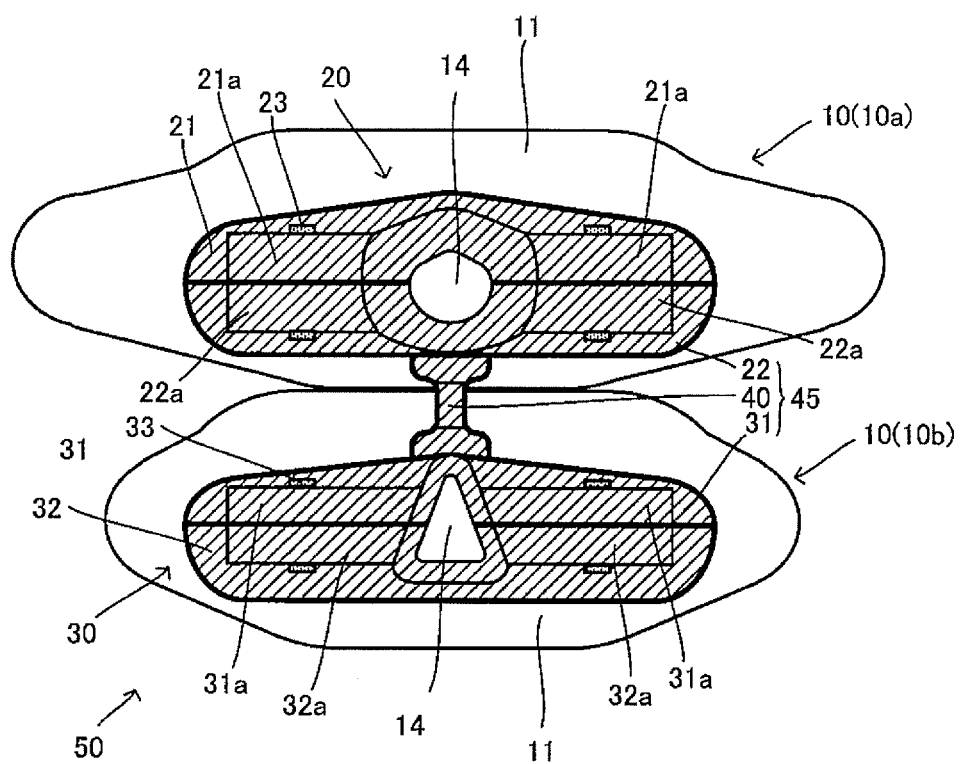
FIG. 4 is a back view schematically illustrating the spine immobilization tool 50 at the posture in which it is mounted on the vertebrae 10 and 10.

FIG. 2 to FIG. 4 are views schematically illustrating a spine immobilization tool 50 according to one embodiment. FIG. 2 is a plan view schematically illustrating the spine immobilization tool 50 at a posture in which it is mounted on the vertebrae 10 and 10. In FIG. 2, the upper side indicates the ventral side, the lower side indicates the back side, the near side indicates the head side, and the far side indicates the buttock side on the plane of paper. FIG. 3 is a side view schematically illustrating the spine immobilization tool 50 at the posture in which it is mounted on the vertebrae 10 and 10. In FIG. 3, the right side indicates the ventral side, the left side indicates the back side, the upper side indicates the head side, and the lower side indicates the buttock side on the plane of paper. FIG. 4 is a back view schematically illustrating the spine immobilization tool 50 at the posture in which it is mounted on the vertebrae 10 and 10. In FIG. 4, the far side indicates the ventral side, the near side indicates the back side, the upper side indicates the head side, and the lower side indicates the buttock side on the plane of paper.

The spine immobilization tool 50 is mounted on a plurality of vertebrae to control the movement of the spine. The spine immobilization tool 50 includes a first covering portion 20, a second covering portion 30, and a joint portion 40. The first covering portion 20 covers at least a part of a vertebral arch 12a of a vertebra 10a at the head side among the adjacent vertebrae, and thus can be fixed to the vertebra 10a. The second covering portion 30 covers at least a part of a vertebral arch 12b of a vertebra 10b at the buttock side among the adjacent vertebrae, and thus can be fixed to the vertebra 10b. The joint portion 40 couples the first covering portion 20 and the second covering portion 30 together while allowing changing relative positions of the first covering portion 20 and the second covering portion 30. Hereinafter, a description will be given of a main portion of these members disposed in the spine immobilization tool 50.

(First Covering Portion 20)

The first covering portion 20 (hereinafter abbreviated as "covering portion 20") includes a first head-side member 21 (hereinafter abbreviated as "head-side member 21") and a first buttock-side member 22 (hereinafter abbreviated as "buttock-side member 22"). The head-side member 21 covers the head side of the vertebral arch 12a. The buttock-side member 22 covers the buttock side of the vertebral arch 12a. The covering portion 20 covers at least a part of the vertebral arch 12a by combining the head-side member 21 and the buttock-side member 22 to sandwich the vertebral arch 12a. Furthermore, as described below, the covering portion 20 has a close-contact surface precisely conforming to the concavo-convex shape of the surface of the vertebral arch 12a. Accordingly, covering at least a part of the vertebral arch 12a with the covering portion 20 allows fixing the covering portion 20 to the vertebra 10a without, for example, screwing the vertebra 10a.

The head-side member 21 includes ear portions 21a and 21a on both lateral sides of the portion in contact with the vertebral arch 12a. The buttock-side member 22 also includes ear portions 22a and 22a on both lateral sides of the portion in contact with the vertebral arch 12a. The head-side member 21 and the buttock-side member 22 are coupled and combined by fixtures 23 and 23 in the ear portions 21a and 21a and the ear portions 22a and 22a. The fixture 23 is not specifically limited insofar as the fixture 23 can couple the head-side member 21 and the buttock-side member 22 together. The fixture 23 can employ, for example, a bolt.

As described above, the covering portion 20 can be fixed to the vertebra 10a by covering at least a part of the vertebral arch 12a. In order to cover the vertebral arch 12a with the covering portion 20 so as to fix the covering portion 20 to the vertebra 10a, the covering portion 20 (each of the head-side member 21 and the buttock-side member 22) has a close-contact surface that has a shape in a male-female relationship with the surface shape of the vertebral arch 12a and can be brought into close contact with the vertebral arch 12a on a surface at a side in contact with the vertebral arch 12a. That is, the covering portion 20 has the close-contact surface shaped precisely conforming to the concavo-convex shape on the surface of the vertebral arch 12a, on the surface at the side in contact with the vertebral arch 12a. The respective vertebral arches of the plurality of vertebrae have mutually different surface shapes. Accordingly, the above-described close-contact surface is shaped corresponding to the surface shape of the vertebral arch in contact with this close-contact surface. The close-contact surface has a varied shape for each covering portion. This configuration of the covering portion 20 with the close-contact surface brings the covering portion 20 into contact with the vertebral arch 12a so as to prevent displacement of the mounting position of the covering portion 20. This facilitates fixing the covering portion 20 to the vertebra 10a.

The manufacturing method of the covering portion 20 is not specifically limited. However, as described above, the covering portion 20 has the above-described close-contact surface on the surface at the side in contact with the vertebral arch 12a. This close-contact surface is manufactured corresponding to the surface shape of the vertebral arch 12a (the vertebra 10a) where the covering portion 20 is to be mounted. In order to manufacture the covering portion 20 to have the close-contact surface in a male-female relationship precisely with the surface of the vertebral arch 12a in the portion in contact with the covering portion 20, for example, three-dimensional surface image data obtained by converting tomographic information of the vertebra 10a into three-dimensional data is used for a publicly-known technique such as the selective laser sintering method, so as to manufacture each member that constitutes the covering portion 20. The device used for the selective laser sintering method employs, for example, "EOSINT M" manufactured by NTT DATA ENGINEERING SYSTEMS Corporation. The tomographic information can be obtained by fluoroscopic measurement or outline measurement using any one type or two or more types of publicly-known methods such as X-ray Computer Tomography (X-ray CT), Magnetic Resonance Imaging (MRI), and ultrasonic photographing in complex association with one another. Here, the manufacturing method of each member that constitutes the covering portion 20 is not limited to the selective laser sintering method. For example, cutting work is available for manufacturing each member. However, the selective laser sintering method is preferred from the aspect of manufacturing the covering portion 20 in a short period of time at low cost.

In the case where the covering portion 20 is manufactured by cutting work, as described below, accumulating the three-dimensional surface image data of various vertebral arches allows shortening the process from the acquisition of the three-dimensional surface image data to the cutting work. That is, firstly, the three-dimensional surface image data of the various vertebral arches is accumulated. Subsequently, these portions of data are categorized by conditions (race, age, gender, height, weight, and similar parameter) of the target. Based on these portions of data, the shape of the vertebral arch is considered for each condition of the patient. A plurality of covering portions with surfaces shaped mostly in a male-female relationship with the considered surface shape of the vertebral arch is preliminarily manufactured. This allows selecting a covering portion appropriate for the vertebral arch before surgery based on the three-dimensional surface image data of the actual vertebral arch of the patient, so as to bring the covering portion into contact with the vertebral arch only by cutting the covering portion a little during surgery. Accordingly, shortening the process from the acquisition of the three-dimensional surface image data to the cutting work allows dealing with the case where this surgical procedure is urgently needed.

The material that constitutes the covering portion 20 is not specifically limited insofar as the covering portion 20 is constituted to have a strength withstanding use and not to provide the negative effect on the living body. This material can employ, for example, titanium, titanium alloy (such as $Ti_6AlV_4$), stainless steel, cobalt-chrome alloy, and tantalum. From the aspect of biocompatibility, titanium and titanium alloy are preferred.

The covering portion 20 is preferred to include a portion (not shown) formed in a mesh-like or sponge-like shape in the portion including the close-contact surface. The term "mesh-like" means a structure with a plurality of holes that pass through from the surface on the side in contact with the vertebral arch 12a (the surface on the ventral side) to the surface on the opposite side (the surface on the back side) in the covering portion 20. The term "sponge-like" means a structure where a plurality of fine cavities is formed inside of the covering portion 20, and may have a structure where these cavities are irregularly continuously formed. The configuration that includes the portion in this mesh-like or sponge-like shape results in formation of fine unevenness in the portion of the covering portion 20 in contact with the vertebral arch 12a, thus improving the fixity when the covering portion 20 is mounted on the vertebral arch 12a.

In the case where the covering portion 20 includes the portion shaped in the mesh-like or sponge-like shape, the close-contact surface and the portion shaped in the mesh-like or sponge-like shape of the covering portion 20 are preferred to employ osteoinductive matrix (not shown). In the case where the configuration employs the osteoinductive matrix on: the surface of the close-contact surface; and the surface or the inside of the through-hole constituting the mesh-like structure, or the surface or the inside of the cavity constituting the sponge-like structure, bone formation occurs on the surface of the covering portion 20 via the portion in the mesh-like or sponge-like shape (that is, autologous bone gets into the portion shaped in the mesh-like or sponge-like shape). This integrates the covering portion 20 and the vertebra 10a together, thus facilitating permanently fixing the covering portion 20 to the vertebra 10a.

Here, "osteoinductive matrix" means a bone prosthetic material or a bone regeneration-promoting substance with a bone regeneration-inducing effect. Materials known as the "bone prosthetic material" includes: a material that has already been approved as medical equipment in Japan for use in a bone defect portion, has approximately the same component with that of the autologous bone, and gradually adhered to and integrated with the autologous bone (for example, hydroxyapatite); and a material that is replaced by the autologous bone (for example, beta-tricalcium phosphate (bTCP)). Materials known as the "bone regeneration-promoting substances" include, for example, bone morphogenetic protein (BMP) as a substance that has the effect of promoting the bone formation.

(Second Covering Portion 30)

The second covering portion 30 (hereinafter abbreviated as "covering portion 30") includes a second head-side member 31 (hereinafter abbreviated as "head-side member 31") and a second buttock-side member 32 (hereinafter abbreviated as "buttock-side member 32"). The second head-side member 31 covers the head side of the vertebral arch 12b. The second buttock-side member 32 covers the buttock side of the vertebral arch 12b. The covering portion 30 covers at least a part of the vertebral arch 12b by combining the head-side member 31 and the buttock-side member 32 to sandwich the vertebral arch 12b. Furthermore, as described below, the covering portion 30 has a close-contact surface precisely conforming to the concavo-convex shape of the surface of the vertebral arch 12b. Accordingly, covering at least a part of the vertebral arch 12b with the covering portion 30 allows fixing the covering portion 30 to the vertebra 10b without, for example, screwing the vertebra 10b.

The head-side member 31 includes ear portions 31a and 31a on both lateral sides of the portion in contact with the vertebral arch 12b. The buttock-side member 32 also includes ear portions 32a and 32a on both lateral sides of the portion in contact with the vertebral arch 12b. The head-side member 31 and the buttock-side member 32 are coupled and combined by fixtures 33 and 33 on the ear portions 31a and 31a and the ear portions 32a and 32a. The fixture 33 is not specifically limited insofar as the fixture 33 can couple the head-side member 31 and the buttock-side member 32 together. The fixture 33 can employ, for example, a bolt.

As described above, the covering portion 30 can be fixed to the vertebra 10b by covering at least a part of the vertebral arch 12b. In order to cover the vertebral arch 12b with the covering portion 30 so as to fix the covering portion 30 to the vertebra 10b, the covering portion 30 (each of the head-side member 31 and the buttock-side member 32) has a close-contact surface that has a shape in a male-female relationship with the surface shape of the vertebral arch 12b and can be brought into close contact with the vertebral arch 12b on a surface at a side in contact with the vertebral arch 12b. That is, the covering portion 30 has the close-contact surface shaped precisely conforming to the concavo-convex shape on the surface of the vertebral arch 12b, on the surface at the side in contact with the vertebral arch 12b. The respective vertebral arches of the plurality of vertebrae have mutually different surface shapes. Accordingly, the above-described close-contact surface is shaped corresponding to the surface shape of the vertebral arch in contact with the close-contact surface. The close-contact surface has a varied shape for each covering portion. This configuration of the covering portion 30 with the close-contact surface allows bringing the covering portion 30 into contact with the vertebral arch 12b so as to prevent displacement of the mounting position of the covering portion 30. This facilitates fixing the covering portion 30 to the vertebra 10b.

The manufacturing method of the covering portion 30 is not specifically limited. However, as described above, the covering portion 30 has the above-described close-contact surface on the surface at the side in contact with the vertebral arch 12b. This close-contact surface is manufactured corresponding to the surface shape of the vertebral arch 12b (the vertebra 10b) where the covering portion 30 is to be mounted. In order to manufacture the covering portion 30 to have the close-contact surface in a male-female relationship precisely with the surface of the vertebral arch 12b in the portion in contact with the covering portion 30, for example, three-dimensional surface image data obtained by converting tomographic information of the vertebra 10b into three-dimensional data is used for a publicly-known technique such as the selective laser sintering method, so as to manufacture each member that constitutes the covering portion 30. The device used for the selective laser sintering method employs, for example, "EOSINT M" manufactured by NTT DATA ENGINEERING SYSTEMS Corporation. The tomographic information can be obtained by fluoroscopic measurement or outline measurement using any one type or two or more types of publicly-known methods such as X-ray Computer Tomography (X-ray CT), Magnetic Resonance Imaging (MRI), and ultrasonic photographing in complex association with one another. Here, the manufacturing method of each member that constitutes the covering portion 30 is not limited to the selective laser sintering method. For example, cutting work is available for manufacturing each member. However, the selective laser sintering method is preferred from the aspect of manufacturing the covering portion 30 in a short period of time at low cost.

In the case where the covering portion 30 is manufactured by cutting work, accumulating the three-dimensional surface image data of various vertebral arches allows shortening the process from the acquisition of the three-dimensional surface image data to the cutting work, similarly to the above-described covering portion 20. This allows dealing with the case where the surgery is urgently needed.

The material that constitutes the covering portion 30 is not specifically limited insofar as the covering portion 30 is constituted to have a strength withstanding use and not to provide the negative effect on the living body. This material can employ, for example, titanium, titanium alloy (such as $Ti_6AlV_4$), stainless steel, cobalt-chrome alloy, and tantalum. From the aspect of biocompatibility, titanium and titanium alloy are preferred.

The covering portion 30 is preferred to include a portion formed in a mesh-like or sponge-like shape (not shown) in the portion including the close-contact surface, similarly to the above-described covering portion 20. Furthermore, in the case where the covering portion 30 includes the portion in the mesh-like or sponge-like shape, similarly to the above-described covering portion 20, the close-contact surface and the portion shaped in the mesh-like or sponge-like shape of the covering portion 30 are preferred to employ osteoinductive matrix (not shown).

(Joint Portion 40)

The joint portion 40 couples the covering portion 20 and the covering portion 30 together. More specifically, the joint portion 40 couples the buttock-side member 22 and the head-side member 31 together. That is, in this embodiment, the buttock-side member 22 and the head-side member 31 are coupled by the joint portion 40 so as to constitute one integrated member 45 (see FIG. 3 and FIG. 4). Thus, the configuration that includes: the head-side member 21; the member 45 that integrates the buttock-side member 22, the head-side member 31, and the joint portion 40 together; and the buttock-side member 32 facilitates attaching and removing the covering portion 20 and covering portion 30 to/from the vertebra 10a and the vertebra 10b, and also facilitates coupling the covering portion 20 and the covering portion 30 by the joint portion 40.

The joint portion 40 is not specifically limited insofar as the joint portion 40 has mobility to allow appropriately changing the relative position between the covering portion 20 and the covering portion 30 and can couple the covering portion 20 and the covering portion 30 together. Here, "mobility to allow appropriately changing" means mobility to the extent that the mobility can be determined as necessary corresponding to the medical condition or similar condition of the patient when using the spine immobilization tool 50. That is, this means that the joint portion 40 has mobility to the extent that the mobility does not apply excessive mechanical stress between adjacent vertebrae while solving the instability with pathological significance. For example, the range of motion of the joint portion 40 can be adjusted or fixed corresponding to the medical condition. This mobility of the joint portion 40 can be adjusted by, for example, the shape of the joint included in the joint portion 40. One joint portion 40 can be constituted by one joint or a combination of a plurality of joints. The mobility of the joint portion 40 can also be adjusted by the number of joints included in the one joint portion 40.

The material that constitutes the joint portion 40 can employ a material similar to those of the covering portion 20 and the covering portion 30 from a similar aspect. The joint of the joint portion 40 can be manufactured from artificial material typified by metal, ceramic, and polyethylene.

(Method for Using Spine Immobilization Tool 50)

The spine immobilization tool 50 can control the movement of the spine by mounting the covering portion 20 on the vertebral arch 12a (the vertebra 10a) and mounting the covering portion 30 on the vertebral arch 12b (the vertebra 10b). For use, the spine immobilization tool 50 is preferred to be sterilized by, for example, gas sterilization or coating.

As described above, the covering portion 20 is divided into the head-side member 21 and the buttock-side member 22. The head-side member 21 and the buttock-side member 22 cover the vertebral arch 12a so as to wrap the vertebral arch 12a from the back side, and the head-side member 21 and the buttock-side member 22 are coupled by the fixtures 23 and 23. Accordingly, the head-side member 21 and the buttock-side member 22 cannot be removed from the vertebra 10a. Thus, covering at least a part of the vertebral arch 12a with the covering portion 20 can fix the covering portion 20 to the vertebra 10a.

The covering portion 30 is divided into the head-side member 31 and the buttock-side member 32, similarly to the covering portion 20. The head-side member 31 and the buttock-side member 32 cover the vertebral arch 12b so as to wrap the vertebral arch 12b from the back side, and the head-side member 31 and the buttock-side member 32 are coupled by the fixture 33 and 33. Accordingly, the head-side member 31 and the buttock-side member 32 cannot be removed from the vertebra 10b. Thus, covering at least a part of the vertebral arch 12b with the covering portion 30 can fix the covering portion 30 to the vertebra 10b.

The buttock-side member 22 (the covering portion 20) and the head-side member 31 (the covering portion 30) are coupled by the joint portion 40. Thus, change in relative position between the vertebra 10a to which the covering portion 20 is fixed and the vertebra 10b to which the covering portion 30 is fixed is controlled by the joint portion 40. Accordingly, the spine immobilization tool 50 can control the movement of the spine. With the spine immobilization tool 50, the change in relative position between the respective vertebrae is controlled by the joint portion 40. Thus, not fixing the spine, but preventing the excessive instability of the spine allows braking the spine.

The spine immobilization tool 50 controls the movement of the spine as described above, and allows transplantation, filling, and injection of, for example, an artificial cushion (such as PVA hydrogel), a cultured intervertebral disc (such as own, allogeneic, or xenogeneic intervertebral disc that is cultured and a stem cell-derived intervertebral disc), and a substance for promoting intervertebral disc regeneration (for example, a bone morphogenetic factor OP-1) for an intervertebral disc.

As described above, the conventional technique may cause various problems due to insertion of, for example, a screw into the vertebra. In contrast, the spine immobilization tool 50 has a structure where the covering portion 20 and the covering portion 30 three-dimensionally and closely wrap the vertebral arch 12a and the vertebral arch 12b. Covering at least a part of the vertebral arch 12a and the vertebral arch 12b with the covering portion 20 and the covering portion 30 prevents the covering portion 20 and covering portion 30 from being removed from the vertebra 10a and the vertebra 10b. Accordingly, the spine immobilization tool 50 prevents the occurrence of various problems that occurs due to insertion of, for example, a screw into the vertebra. That is, the spine immobilization tool 50 is safe and secure, and has a low possibility of occurrence of additional lesion. However, in the spine immobilization tool of the present invention, a fixing member such as a spinal fixation screw for fixing the covering portion to the vertebra can be used for assistance. Fixing the covering portion to the vertebra using the fixing member allows more strongly fixing the covering portion to the vertebra. Thus, use of the spinal fixation screw for assistance ensures the reduced number of spinal fixation screws compared with the conventional number, and ensures reduced depth of insertion compared with the conventional depth. This ensures high safety and prevents occurrence of additional lesion.

The covering portion 20 and the covering portion 30 are removably attachable to the vertebra 10a and the vertebra 10b. Accordingly, a publicly-known technique such as the selective laser sintering method can be used for manufacturing a precise model of, for example, the spine (the vertebra 10a and the vertebra 10b), in order to perform, for example, surgical simulation for mounting the covering portion 20 and the covering portion 30 using this model before surgery or in order to perform biological evaluation for predicting the spine movement after surgery.

(Other Configurations)

Figure 5:
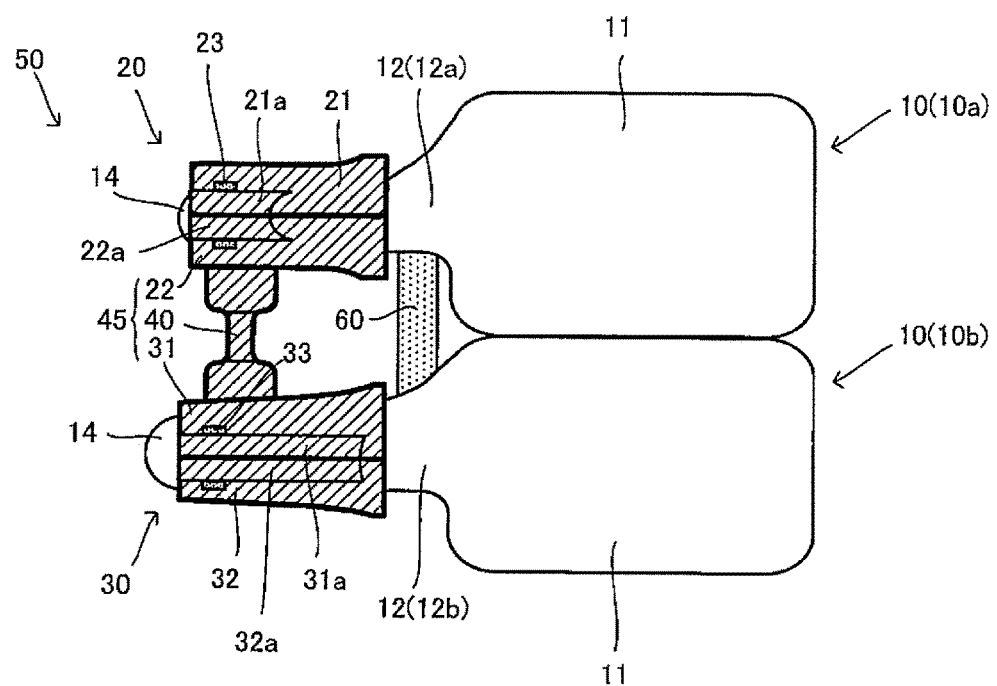
FIG. 5 is a view schematically illustrating a usage example in the case where the spine immobilization tool 50 is used in order to temporarily immobilize a spine, and is a view corresponding to FIG. 3.

In the description of the above spine immobilization tool 50, the covering portions 20 and 30 have been described as the example preferred for permanently fixing to the vertebrae 10*a* and 10*b*. However, the usage of the spine immobilization tool of the present invention is not limited to this method. For example, the spine immobilization tool of the present invention may be used in order to temporarily immobilize or fix the spine. FIG. 5 is a view schematically illustrating a usage example in the case where the spine immobilization tool 50 is used in order to temporarily immobilize the spine, and is a view corresponding to FIG. 3.

In the case where the spine immobilization tool 50 is used in order to temporarily immobilize or fix the spine, as illustrated in FIG. 5, an elastic tissue 60 such as an autologous bone taken from, for example, ilium bone, an autologous intervertebral disc, an allogeneic bone, an allogeneic intervertebral disc, and a synthetic and cultured intervertebral disc tissue is transplanted to fix the relative position between the vertebral arches on which the spine immobilization tool 50 is mounted. After fusion of the tissue 60 and the vertebral arch, the spine immobilization tool 50 is removed. The spine immobilization tool 50 is used in order to temporarily immobilize the spine on the premise that the spine immobilization tool 50 is removed from the vertebral arch afterward. Therefore, to facilitate the removal of the spine immobilization tool 50, the covering portions 20 and 30 are preferred not to include the portion in the mesh-like or sponge-like shape or the osteoinductive matrix described above.

Figure 6:
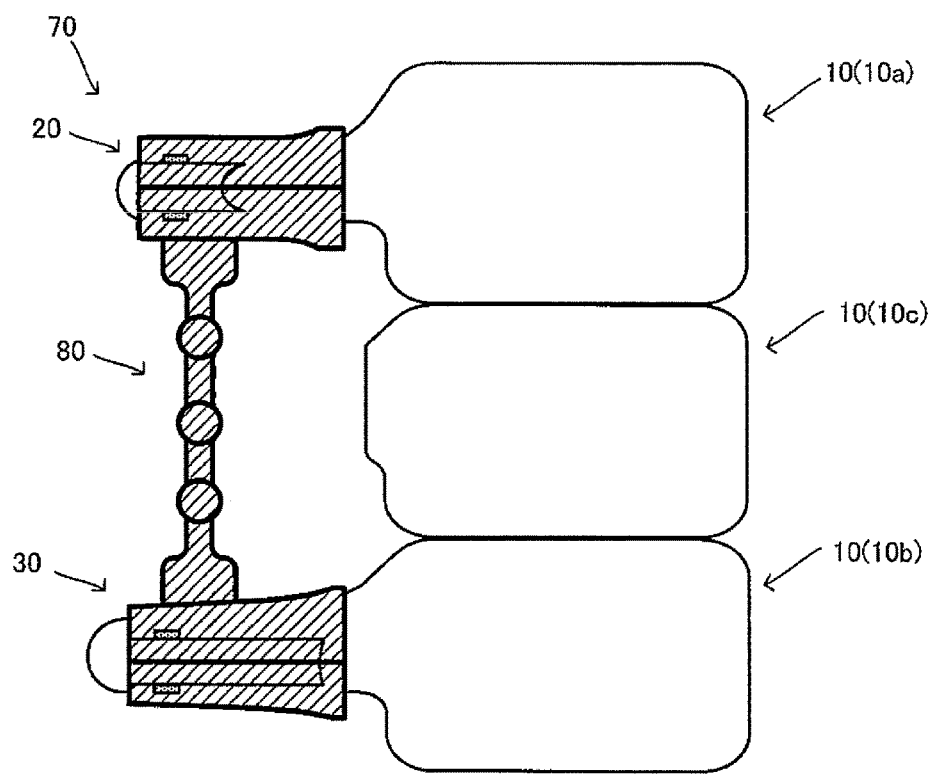
FIG. 6 is a view schematically illustrating a spine immobilization tool 70 according to another embodiment, and is a view corresponding to FIG. 3.

While in the description of the spine immobilization tool 50 so far, the configuration where the spine immobilization tool 50 is mounted on the adjacent vertebrae has been described as the example, the present invention is not limited to this configuration. FIG. 6 is a view schematically illustrating a spine immobilization tool 70 according to another embodiment, and is a view corresponding to FIG. 3.

The spine immobilization tool 70 illustrated in FIG. 6 includes the covering portion 20, the covering portion 30, and a joint portion 80 that couples the covering portion 20 and the covering portion 30 together. In this embodiment, another vertebra 10*c* lies between the vertebra 10*a* on which the covering portion 20 is mounted and the vertebra 10*b* on which the covering portion 30 is mounted. Thus, in the spine immobilization tool 70, the covering portion 20 and the covering portion 30 are mounted on respective vertebrae apart from each other. Accordingly, the joint portion 80 is long compared with the above-described joint portion 40. On the other hand, the conditions other than the length are similar to those of the joint portion 40. Thus, detailed description is omitted. That is, the joint portion 80 can also adjust the mobility by the shapes or the number of joints included in the joint portion 80, similarly to the joint portion 40. In the case where the covering portions are mounted on the vertebrae apart from each other like the spine immobilization tool 70, the vertebral arch and similar part is preferred to be cut away from the vertebra 10*c* on which the covering portion is not mounted so as not to hinder the mounting of the spine immobilization tool 70 or the movement of the joint portion 80.

While in FIG. 6 the spine immobilization tool 70 with the configuration where the covering portions are mounted at an interval of one vertebra has been described as the example, the spine immobilization tool of the present invention may employ a configuration where the covering portions are mounted on vertebrae apart from each other at an interval of two or more vertebrae.

Figure 7:
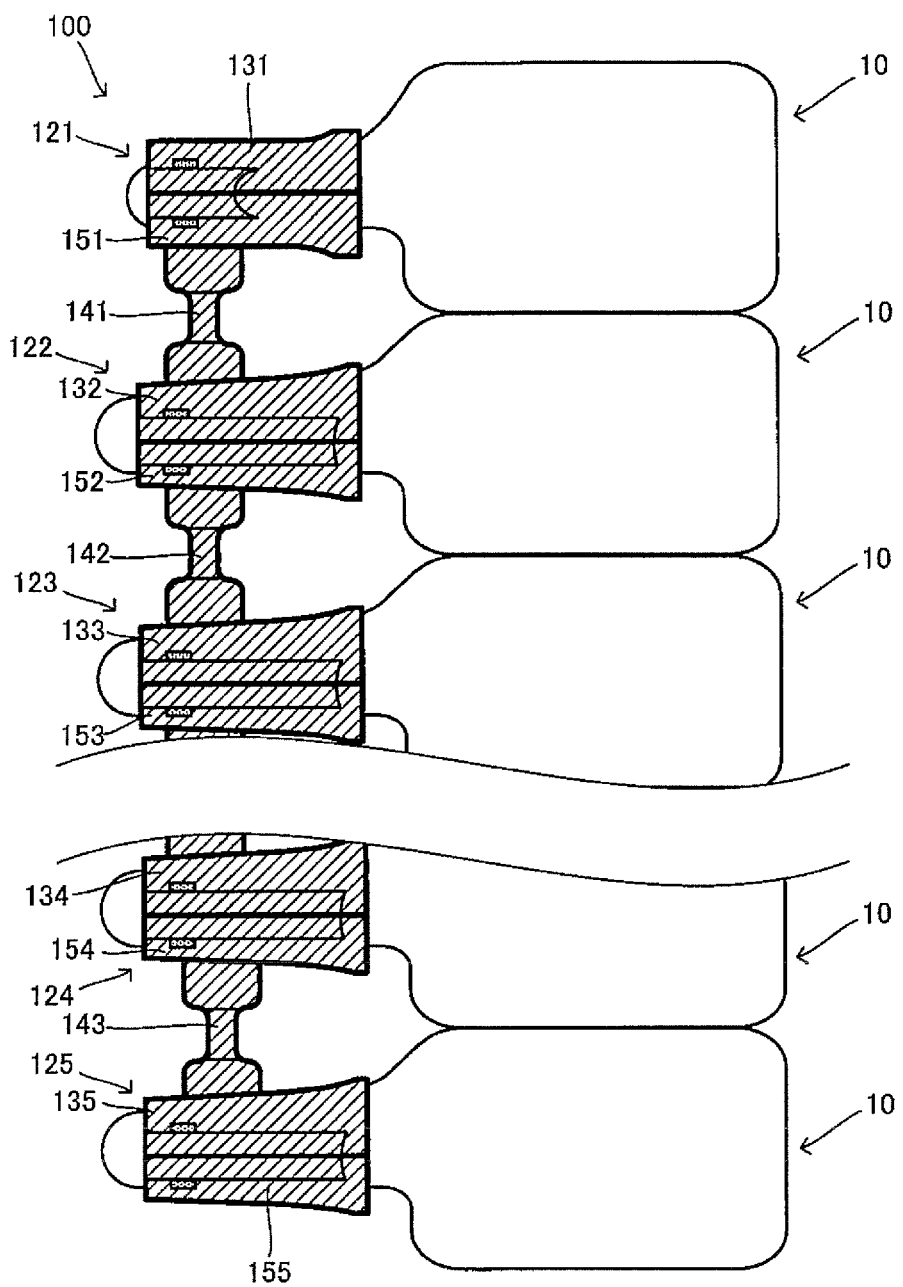
FIG. 7 is a side view schematically illustrating a spine immobilization tool 100 at a posture in which it is mounted on the vertebrae 10 to 10.

While in the description of the present invention so far, the configuration that includes two covering portions has been described as the example, the spine immobilization tool of the present invention is not limited to this configuration. The spine immobilization tool of the present invention may employ a configuration that includes three or more covering portions. That is, mounting the covering portions on three or more vertebrae also allows immobilizing the spine. FIG. 7 is a side view schematically illustrating a spine immobilization tool 100 according to another embodiment. FIG. 7 schematically illustrates a part of the spine immobilization tool 100 at a posture in which it is mounted on the vertebrae 10 to 10. In FIG. 7, the right side indicates the ventral side, the left side indicates the back side, the upper side indicates the head side, and the lower side indicates the buttock side on the plane of paper.

The spine immobilization tool 100 mounted on the plurality of vertebrae 10 to 10 can control the movement of the spine. The spine immobilization tool 100 includes covering portions 121 to 125 that can be fixed to the vertebrae 10 to 10 by covering at least a part of the vertebral arches of the vertebrae 10 to 10 for the respective plurality of vertebrae 10 to 10. Among the covering portions 121 to 125, the adjacent covering portions are coupled together by the joint portions 141 to 143 to allow changing the respective relative positions. The covering portions 121 to 125 each includes the head-side members 131 to 135 that each covers the head side of the vertebra 10 and the buttock-side members 151 to 155 that each covers the buttock side of the vertebra 10. Among the vertebrae 10 to 10 on which the spine immobilization tool 100 is mounted, the covering portion 121 that can be fixed to the vertebra closest to the head side is assumed to be a first covering portion. Among the vertebrae 10 to 10 on which the spine immobilization tool 100 is mounted, the covering portion that can be fixed to the n-th vertebra from the head side (here, n is a natural number equal to or more than 2) is assumed to be the n-th covering portion. In this case, the buttock-side members 151 to 155 of the n'-th covering portion (here, n' is a natural number from 1 to n−1), the head-side members 132 to 135 of the (n'+1)-th covering portion, and the joint portions 141 to 143 are integrated with one another. The joint portions 141 to 143 couple the buttock-side members 151 to 155 of the n'-th covering portion and the head-side members 132 to 135 of the (n'+1)-th covering portion together.

In the spine immobilization tool 100, the joint portions 141 to 143 can employ a configuration similar to that of the joint portion 40 or the joint portion 80. Thus, detailed description is omitted. The covering portions 121 to 125 are shaped to have an appropriate configuration corresponding to the respective positions to be arranged. Therefore, the positions in which the joint portions 141 to 143 are disposed, the shapes of the surfaces at the side in contact with the vertebral arch, and similar parameter are different from one another. However, the configuration can be mostly similar to that of the covering portion 20. Thus, detailed description is omitted.

In the description of the spine immobilization tool of the present invention so far, the configuration where a part of one covering portion and a part of the other covering portion among the adjacent covering portions are integrated together via the joint portion has been described as an example. However, the spine immobilization tool of the present invention is not limited to this configuration. The spine immobilization tool of the present invention may employ a configuration where the covering portion and the joint portion are separately shaped, and the joint portion may be removably attachable to the covering portion. Employing this configuration allows firstly fixing the covering portion to the vertebra and then coupling the adjacent covering portions together by the joint portion. For example, a plurality of covering portions that are independently shaped are fixed to the respective vertebrae, and the autologous bone permanently fixes the covering portions to the vertebrae after a lapse of a predetermined time period. Subsequently, the adjacent covering portions can be coupled by the joint portion.

While in the description of the spine immobilization tool of the present invention so far, the configuration where the covering portion includes the head-side member and the buttock-side member has been described as an example, the spine immobilization tool of the present invention is not limited to this configuration. In the spine immobilization tool of the present invention, the covering portion is not specifically limited insofar as the covering portion has a configuration in which the covering portion is removably attachable to the vertebra and can fix the relative position with respect to the vertebra when being mounted on the vertebra so as to cover at least a part of the vertebral arch in the vertebra. For example, while in the description of the present invention so far, the configuration where two members that constitute the covering portion sandwich the vertebral arch in the vertical direction has been described, in the present invention, the number of members that constitute the covering portion and the direction to sandwich (wrap) the vertebral arch by these members are not specifically limited. However, from the aspect of ease of, for example, attaching and removing the covering portion to/from the vertebra, the configuration where the covering portion is separately shaped by the head-side member and the buttock-side member is preferred.

In the description of the spine immobilization tool of the present invention so far, the configuration where the head-side member and the buttock-side member are coupled together by the fixtures in the ear portions has been described as an example. However, the spine immobilization tool of the present invention is not limited to this configuration. In the spine immobilization tool of the present invention, in the case where the covering portion is constituted of a plurality of members and the plurality of members is combined together so as to cover the vertebral arch by the covering portion as a configuration, the method for combining the plurality of members is not specifically limited. For example, a configuration that can combine the respective members together by fitting these members is possible.

DESCRIPTION OF REFERENCE SIGNS 10, 10a, 10b, 10c vertebra
11 vertebral body
12, 12a, 12b vertebral arch
13 transverse process
14 spinous process
15 vertebral foramen
20 first covering portion
21 first head-side member
21a ear portion
22 first buttock-side member
22a ear portion
23 fixture
30 second covering portion
31 second head-side member
31a ear portion
32 second buttock-side member
32a ear portion
33 fixture
40, 80 joint portion
50, 70, 100 spine immobilization tool
60 elastic tissue

I claim:
1. A method for producing a spine immobilization tool that can control movement of a spine by being mounted on a plurality of vertebrae, the method comprising:
   obtaining three-dimensional shape data of at least a part of a vertebral arch of each of the vertebrae;
   producing a plurality of covering portions based on the obtained three-dimensional shape data, each of the covering portions being fixable to one of the plurality of vertebrae by covering at least a part of the vertebral arch and exposing at least a distal portion of a spinous process; and
   coupling, by a joint portion adjacent ones of the covering portions such that a relative position between the adjacent covering portions is allowed to be changed, the joint portion being disposed between the adjacent covering portions,
   wherein in said producing a plurality of covering portions, each of the covering portions is produced so as to have a close-contact surface that has a shape in a male-female relationship with a surface shape of the vertebral arch, the close-contact surface being allowed to be in close contact with the vertebral arch,
   wherein each covering portion further including a head-side member and a buttock-side member each containing an ear portion,
   wherein the head-side member and the buttock-side member are fixable to the vertebra in a manner to cover a 360 degree surround area of a part of the spinous process by at least the part of the vertebral arch sandwiched by both the head-side member and the buttock-side member, and
   wherein a fixture is penetrated into both the ear portion of the head-side member, and the ear portion of the buttock-side member in a direction where at least the part of the vertebral arch is sandwiched by both the head-side member and the buttock-side member, so that the head-side member and the buttock-side member are coupled and combined.

2. The method for producing a spine immobilization tool according to claim 1, wherein the three-dimensional shape data is obtained from tomographic information of the vertebra.

3. The method for producing a spine immobilization tool according to claim 1, wherein the covering portions are produced with a selective laser sintering method.

4. The method for producing a spine immobilization tool according to claim 1, wherein the covering portions are produced by cutting work.

5. The method for producing a spine immobilization tool according to claim 1, wherein a portion of each of the covering portions is shaped in mesh-like or sponge-like, the portion including the close-contact surface.

6. The method for producing a spine immobilization tool according to claim 5, wherein the portion shaped in mesh-like or sponge-like employs osteoinductive matrix.

7. The method for producing a spine immobilization tool according to claim wherein
   the head-side member includes ear portions on both lateral sides of the portion in contact with the vertebral arch, and
   the buttock-side member includes ear portions on both lateral sides of the portion in contact with the vertebral arch.

* * * * *